United States Patent [19]
Lloyd et al.

[11] Patent Number: 5,493,127
[45] Date of Patent: Feb. 20, 1996

[54] FEEDBACK CONTROL OF ELECTRORHEOLOGICAL FLUID RESPONSE

[75] Inventors: John R. Lloyd, East Lansing; Clark J. Radcliffe, Okemos, both of Mich.

[73] Assignee: Michigan State University, East Lansing, Mich.

[21] Appl. No.: 359,589

[22] Filed: Dec. 20, 1994

[51] Int. Cl.⁶ .................................................. G01N 21/49
[52] U.S. Cl. ........................ 250/573; 250/574; 356/436
[58] Field of Search ................................. 250/573, 574, 250/576; 356/432, 436

[56] References Cited

U.S. PATENT DOCUMENTS

| | | |
|---|---|---|
| 4,384,761 | 5/1983 | Brady et al. . |
| 4,406,513 | 9/1983 | Raphael . |
| 4,582,391 | 4/1986 | Legrand . |
| 4,786,128 | 11/1988 | Birnbach . |
| 4,799,234 | 1/1989 | Haeussler et al. . |
| 4,843,248 | 6/1989 | Miyata et al. ........................... 250/574 |
| 5,020,872 | 6/1991 | DuPuy et al. . |
| 5,194,921 | 3/1993 | Tambo et al. ........................... 356/432 |
| 5,387,971 | 2/1995 | Koashi et al. ........................... 356/246 |
| 5,409,435 | 4/1995 | Daniels ........................................ 482/5 |

*Primary Examiner*—Edward P. Westin
*Assistant Examiner*—Stephen Calogero
*Attorney, Agent, or Firm*—Brooks & Kushman

[57] ABSTRACT

A closed loop feedback control for enhancing the response of electrorheological fluid having a light source and a photodetector measuring the light transmission through the electrorheological fluid. A manually controllable signal generator generates a reference signal indicative of the desired transmission through the electrorheological fluid. A control amplifier responsive to the difference between the measured transmission and the reference signal changes the value of the electric field being applied across the electrorheological. The change in the electric field selected to significantly reduce the time required for the electrorheological fluid to change from its current state to the desired state.

25 Claims, 3 Drawing Sheets

5,493,127

FEEDBACK CONTROL OF ELECTRORHEOLOGICAL FLUID RESPONSE

TECHNICAL FIELD

The invention is related to the control of the state of electrorheological fluids and, in particular, to a feedback control of electrorheological fluid response from an initial state to a desired state.

BACKGROUND ART

An electrorheological fluid is typically formed of a suspension of hydrophilic particles in a hydrophilic liquid. When an electric field is applied across the electrorheological fluid, the particles form chains parallel to the electric field changing properties such as: the viscosity, stiffness, thermal conductivity and optical transmission of the electrorheological fluid. In past applications, the control of the electrorheological fluids has been "open-loop", in which an electric field was applied to control the viscosity, stiffness, thermal conductivity or optical transmission of the electrorheological fluid. These "open-loop" approaches to control the state of the electrorheological fluid have been hampered by the strongly time-dependent and non-linear behavior of the electrorheological fluids. Short periods between field activation yield strong action, while periods of inactivity yield slower and weaker action because the particles in the electrorheological fluid scatter with time.

The effects of temperature and humidity also contribute to a wide variation in open-loop speed and strength of response. The inventors have identified a mechanism by which closed loop feedback of one of the physical properties of the electrorheological fluid can be used to increase the response of the electrorheological to a change from a current state to a desired state and precisely control the properties of the electrorheological fluid such as the viscosity, the stiffness, the thermal conductivity or the optical transmission of the electrorheological fluid.

SUMMARY OF THE INVENTION

The invention is an apparatus and method for the control of an electrorheological fluid using feedback indicative of at least one parameter of the electrorheological fluid. The control has an electro optical system for measuring the optical transmission and/or the reflection properties of the electrorheological fluid to generate a current state signal having a value corresponding to the transmission or reflection characteristic of the electrorheological fluid. A signal generator generates a reference signal indicative of the desired state of the electrorheological fluid and a control amplifier generates an electric field across the electrorheological fluid. The electric field controls the current state of the electrorheological fluid. The control amplifier's electric field is proportional to the reference signal and holds the fluid at its current state. The control amplifier's electric field is further responsive to the difference between the desired and current state signals. Thus, a change in desired state causes a large change in control amplifier field until the desired state is reached. This large change in field increases the speed and accuracy of changes in fluid state between current and new desired states.

In the preferred embodiment, the electro optical control system uses a light source to produce a light beam through the electrorheological fluid and a—detector for sensing the intensity of the light beam after having passed through the electrorheological fluid. The detector generates a current state signal having a value indicative of the transmission or reflection of the electrorheological fluid.

One advantage of the closed loop feedback control is that it can increase or decrease the response time of the electrorheological fluid.

Another advantage is that the closed loop feedback control precisely controls the state of the electrorheological fluid.

Still another advantage is that the closed loop feedback control of the optical transmission of the electrorheological fluid also controls the state of the electrorheological fluid and may be used to control the viscosity, stiffness and thermal conductivity.

These and other advantages of the closed loop feedback control of electrorheological fluids will become more apparent from a reading of the detailed description of the invention in conjunction with the drawings.

DETAILED DESCRIPTION OF THE INVENTION

Figure 1:
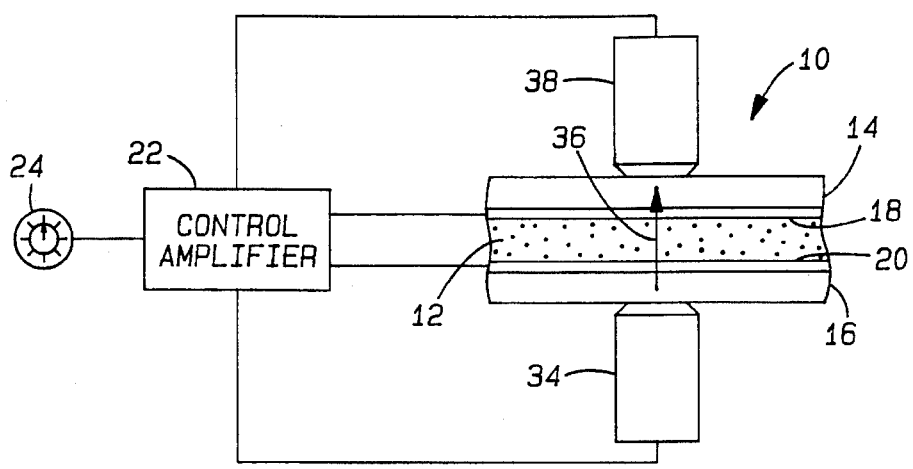
FIG. 1 is a drawing illustrating a first embodiment of the feedback control.
Figure 2:
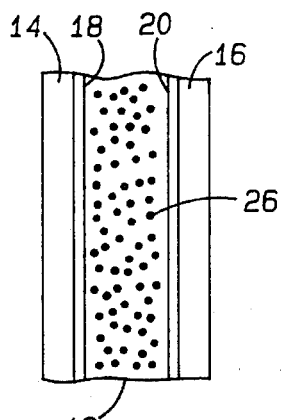
FIG. 2 is a cross-section illustrating a disordered state of the electrorheological fluid.

The details of the closed loop control of the fluid properties of electrorheological (ER) fluids are shown in FIGS. 1 through 6. The device using the electrorheological fluid may be a variable transmission window, an electronically controlled shock absorber for vehicles electronically controlled vibration mounts or other applications. In the embodiment shown in FIG. 1, a variable transmission window 10 has an electrorheological fluid 12 disposed between two substantially parallel transparent windows 14 and 16. In the following discussions, the electrorheological fluid controls the transmission of the electrorheological fluid 12 disposed between the two transparent windows 14 and 16. The windows 14 and 16 may be glass or any suitably transparent plastic or other material. The windows 14 and 16 are coated, on the surface interfacing with the electrorheological fluid, with transparent conductive electrodes 18 and 20, respectively, such as a tin oxide, indium tin oxide, or other suitable transparent conductive coating.

A controller 22 provides a potential difference between the transparent conductive electrodes 18 and 20, creating an electric field across the electrorheological fluid 12. This potential may be a DC or AC potential. As is known in the art, the viscosity, thermal conductivity, the thermal and optical transmission and the reflectivity of the electrorheological fluid will change as a function of the strength of the applied electric field.

Figure 3:
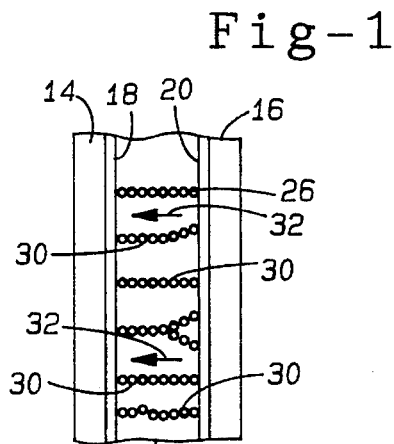
FIG. 3 is a cross-section illustrating an ordered state of the electrorheological fluid in response to a high voltage electric field.

An electrorheological fluid is a suspension of micron-size dielectric particles 26 suspended in a transparent fluid 28 having a different dielectric constant. In the absence of a high voltage electric field, the dielectric particles 26 exist in a disordered colloidal state as pictorially illustrated in FIG. 2. In the presence of a high voltage electrical field, the electrorheological undergoes a transition from the disorder colloidal state to an ordered pseudo solid state, typically characterized by fibrous columns 30 of dielectric particles 26 aligned along the field lines 32, as shown in FIG. 3. The electrorheological fluid has a minimum optical transmission when in the disordered colloidal state and a maximum optical transmission when in the ordered pseudo solid state.

The electrorheological fluid 12 may be made from various combinations of particles and suspension fluids. One electrorheological fluid which has been found to work well in a variable transmission window is made from micron-size crystalline zeolite particles, suspended in phenylmethyl polysiloxane silicon oil. The zeolite particles are substantially neutrally buoyant in the silicon oil which ensures a relatively homogenous composition over an extended period of time.

Returning to FIG. 1, a light source such as a laser 34 produces a light beam 36 having a known intensity through the electrorheological fluid 12 at a predetermined angle relative to the electrical field lines. Preferably, the light beam 36 is parallel to the electrical field lines as shown. The light beam 36 transmitted through the electrorheological fluid is detected by a photodetector 38. The output of the photodetector 38 is a current state signal having a value indicative of the current physical state of the electrorheological fluid. The value of the current state signal is governed by the transmission of the laser light beam through the electrorheological fluid 12. This current state signal is communicated to the control 22 where it is compared with a reference signal generated by a selector control 24. The reference signal generated by the selector control 24 is manually variable and has a value indicative of a desired physical state of the electrorheological fluid, i.e. optical transmission, of the light beam 36 through the electrorheological fluid 12 or the reflection properties of the electrorheological fluid.

The control 22 will respond to the difference between the value of the current state signal generated by the photodetector 38 and the reference signal generated by the selector control 24 and will control the magnitude of the high voltage electric field applied across the electrorheological fluid 12 until the current state signal is equal to the reference signal.

The control 22 will change the voltage between the transparent conductive electrodes 18 and 20 as a function of the value of the reference signal and the difference between the value of the current state signal and the reference signal. The current state signal is, as previously indicated, a measure of the physical properties of the electrorheological fluid and the function at which the potential difference between the electrodes 18 and 20 is changed to generate the high voltage field required to quickly achieve and precisely maintain the properties of the electrorheological fluid 12 indicated by the value of the reference signal. The control 22 generates a high strength electric field when the difference between the current state signal and the reference signal is large and continuously lowers the strength of the electric field to exactly the level required to maintain the desired optical transmission, viscosity, stiffness or thermal conductivity as the difference between the current state signal and the reference signal approaches zero (0) as indicated by curve 44 in FIG. 4.

Because the optical transmission optical reflectance, stiffness, fluid viscosity and thermal transmission are a direct function of the particle organization in the electrorheological fluid 12, the measurement of the optical transmission or reflectance is a direct measure of the particle organization in the electrorheological fluid. This closed loop control of the fluid properties of the electrorheological fluid 12 permit the use of the electrorheological fluids in a wide variety of applications where the lack of fast, precise control limited their past use. A few examples of where the closed loop control of the fluid properties of electrorheological fluids may be used include electronically controlled shock absorbers for vehicles, electronically controlled vibration mounts or dampers, windows having controlled optical transmission, or walls or panels having electronically controlled thermal conductivity.

Figure 4:
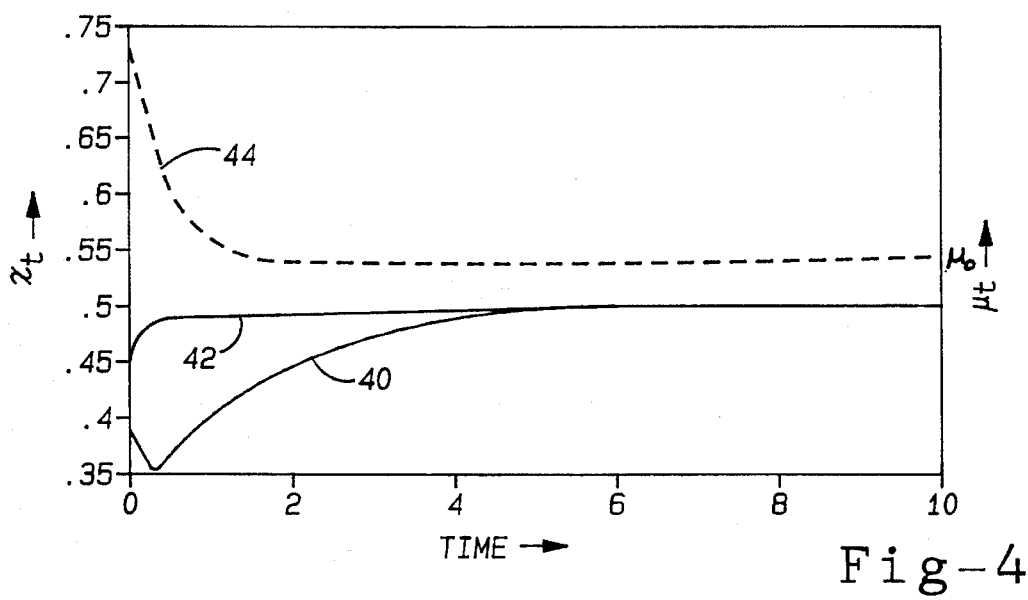
FIG. 4 is a graph illustrating the response of the electrorheological fluid with and without feedback.

The advantages of the closed loop control of the physical properties of an electrorheological fluid are illustrated in FIG. 4. The curve 40 represents the change in the ordered pseudo solid state x(t) of the electrorheological fluid in response to a constant electric field 40 while curve 42 represents the change in the ordered pseudo solid state of the electrorheological fluid using feedback to enhance the fluid's response characteristics. Curve 44 as previously discussed represents the change in the potential difference between electrodes 18 and 20 produced by the feedback control. The value of the voltage difference between transparent electrodes 18 and 20, i.e. the value of the high voltage electric field (u) applied across the electrorheological fluid 12 used to generate the response curve 36 is increased from its initial value $\mu_o$ the value of the current state signal ($x_t$) and the value of the reference signal ($x_{ref}$) as indicated below:

$$U = \mu_o + K_p (X_{ref} - X_t)$$

where $K_p$ is the proportional feedback gain of the control 22.

As indicated by the difference between curves 40 and 42, the feedback of the transmission signal in combination with the proportional gain ($K_p$) generates a substantial increase in the speed of the response of the electrorheological fluid from a current state to a desired state with no modification in the physics of the controlled electrorheological fluid. All the changes in the response arise from the feedback action of the controller made possible by the measurement of the transmission through, i.e. the sensed state of, the electrorheological fluid. As would be obvious to those skilled in the art, the excess increase in the strength of the electric field decays to zero when the difference between the current state signal and the reference signal approaches zero.

Figure 5:
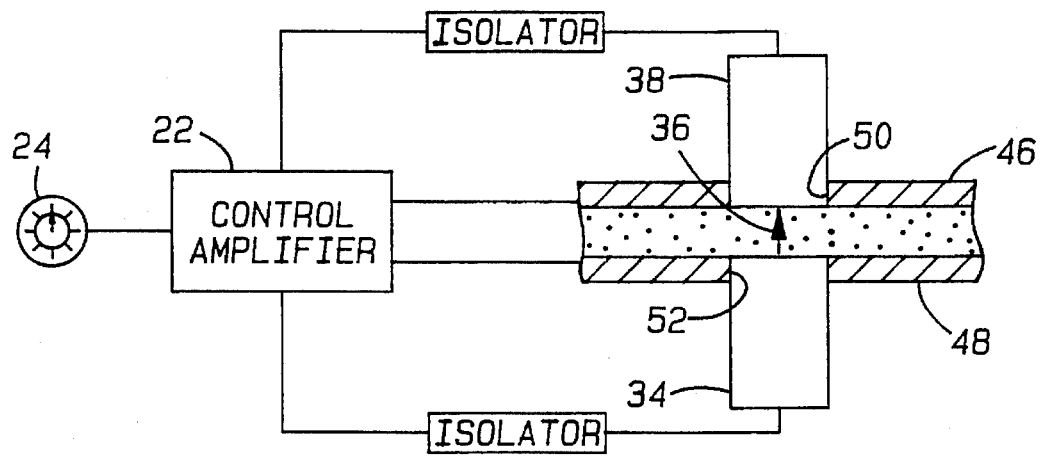
FIG. 5 is a drawing illustrating a second embodiment of the feedback control.
Figure 6:
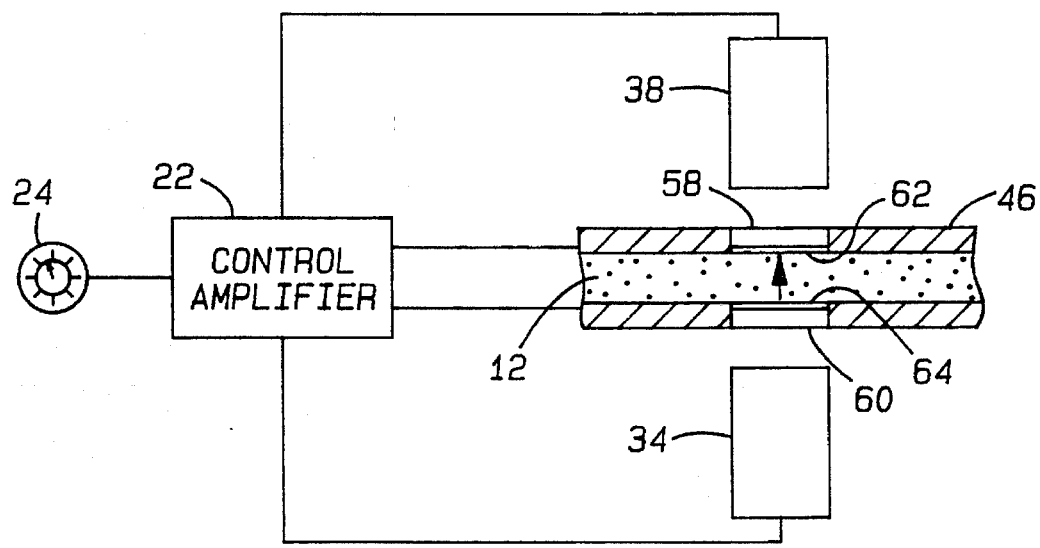
FIG. 6 is a drawing illustrating a third embodiment of the feedback control.

The laser 34 and the detector 38 may also be used in combination for the closed loop control of the fluid properties of an electrorheological fluid where the electrodes are optically opaque metal elements as shown in FIGS. 5 and 6.

Referring to FIG. 5, electrorheological fluid 12 is bounded by metal electrodes 46 and 48, which are connected respectively to the high voltage outputs of the control 22. The metal electrode 46 has a first aperture 50 in which is received the detector 38 while the metal electrode 48 has a second aperture 52 coaxially aligned with the first aperture 50. The light source 34 is mounted directly in the second aperture 52 in coaxial alignment with the photodetector 38 such that the laser beam 36 is directed toward the photodetector 38 parallel to the electric field lines.

A reference signal generator, such as the manually variable selector control 24 generates a reference signal having a value corresponding to a desired transmission value. The control amplifier 22 will control the voltages applied to the metal electrodes 40 and 42 to increase the response of the electrorheological fluid 12 from a given state to the desired state. As is known in the art, optical isolators 54 and 56, may be required to electrically isolate the control amplifier 22 from the high voltages of the laser 34 and the photodetector 38 attached to the metal electrodes 40 and 42.

As shown in FIG. 6, optically transparent windows 58 and 60 may be provided through the metal electrodes 40 and 42, respectively, and the laser 34 and photodetector 38 may be displaced from and electrically insulated from the electrodes 58 and 60 as shown. The windows 58 and 60 effectively eliminate the need for the optical isolators 54 and 56 shown in FIG. 5. In order to prevent a perturbation of the electrical field in the vicinity of the windows 58 and 60, the surfaces of the windows interfacing the electrorheological fluid 12 may be coated with transparent, electrically conductive coatings 62 and 64, respectively, as described relative to FIG. 1.

Figure 7:
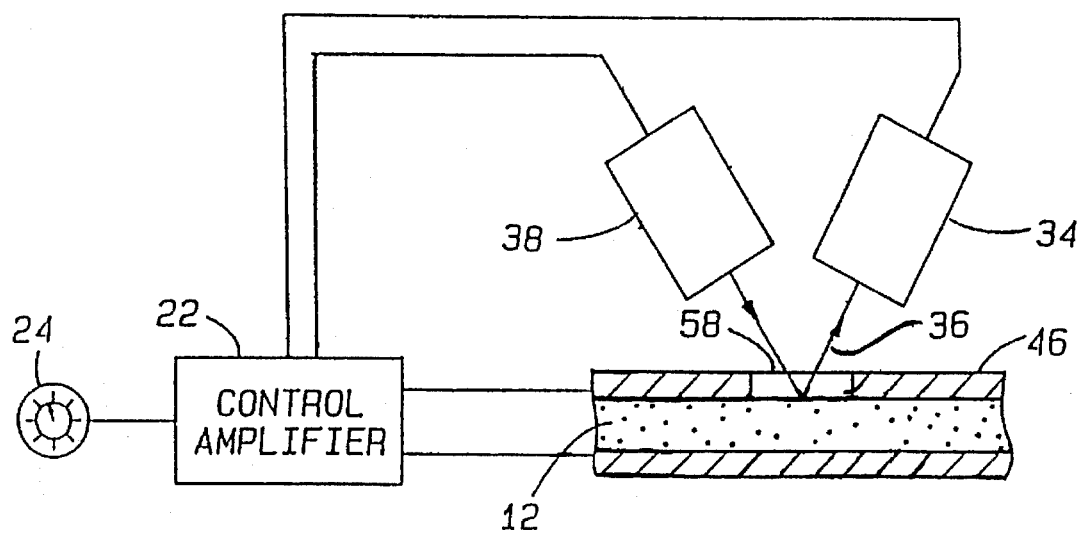
FIG. 7 is a drawing illustrating a fourth embodiment of the feedback control.

Alternatively, as shown in FIG. 7, the light source 34 and the detector 38 may be placed on the same side of the metal electrode 46. In this embodiment, the light source 34 and the detector are disposed at an angle relative to the surface of the electrorheological fluid 12. The light source 34 and the detector are arranged so that the light beam transmitted through the window 58 is reflected by the surface of the electrorheological fluid is received by the detector 38. Anti-reflection coatings on the window 58 would reduce the reflections by these surfaces.

While the best mode for carrying out the invention has been described in detail, those familiar with the art to which this invention relates will recognize various alternative designs and embodiments for practicing the invention as defined by the following claims.

What is claimed is:

1. A feedback control of electrorheological fluid response, comprising:

means for measuring at least one parameter of said electrorheological fluid to generate a current state signal indicative of the current physical state of said electrorheological fluid;

a signal generator for generating a reference signal indicative of a desired value of said at least one parameter;

a control amplifier generating an electric field across said electrorheological fluid, said control amplifier responsive to said reference signal and the difference between said current state signal and said reference signal to generate a change in said electric field across said electrorheological fluid selected to reduce the response time of said at least one parameter of said electrorheological fluid to a change from said current physical state to said desired value.

2. The feedback control of claim 1 wherein said at least one parameter is the optical transmission of said electrorheological fluid at a predetermined angle to the field lines of said electric field.

3. The feedback control of claim 2 wherein said predetermined angle is parallel the said field lines of said electric field.

4. The feedback control of claim 2 wherein said means for measuring comprises a light source disposed on one side of said electrorheological fluid generating a light beam through said electrorheological fluid and a detector disposed on the opposite side of said electrorheological fluid to generate said current state signal having a value indicative of the transmission of said light beam through said electrorheological fluid.

5. The feedback control of claim 4 wherein said control amplifier generates a change in said electric field proportional to the difference between said current state signal and said reference signal.

6. The feedback control of claim 4 wherein said electrorheological fluid is captivated between a pair of spatially separated electrodes and said control amplifier generates high voltage signals applied to said spatially separated electrodes to generate said electric field across said electrorheological fluid.

7. The feedback control of claim 6 wherein said spatially separated electrodes are transparent electrically conductive electrodes disposed on the surface of said spatially separated transparent windows.

8. The feedback control of claim 6 wherein said pair of spatially separated electrodes are opaque metal electrodes, one electrode of said pair of opaque electrodes having a first aperture receiving said light source and the other electrode of said pair of electrodes having a second aperture coaxially aligned with said first aperture and receiving said photodetector.

9. The feedback control of claim 6 wherein said pair of spatially separated electrodes comprises a pair of spatially separated opaque metal electrodes, each metal electrode having a window provided there-through, coaxial with each other permitting said light beam to be transmitted from said light source to said photodetector through said coaxial windows and said electrorheological fluid.

10. A feedback control of electrorheological fluid response, comprising:

a pair of spatially separated electrodes;

an electrorheological fluid filling the space between said pair of spatially separated electrodes;

a light source for generating a light beam through said electrorheological fluid at a predetermined angle to an electric field through said electrorheological fluid;

means for detecting the intensity of said light beam transmitted through said electrorheological fluid to generate a current state signal having a value indicative of the current state of said electrorheological fluid;

a controllable signal generator for generating a reference signal having a value indicative of a desired state of said electrorheological fluid;

a controller for applying an electric potential between said spatially separated electrodes to generate said electric field, said controller responsive to the difference between said current state signal and said reference signal for changing said electric potential between said pair of spatially separated electrodes to change the value of said electric field being applied across said electrorheological fluid, said changing of said electric potential reducing the time required for said electrorheological fluid to change from said current state to said desired state.

11. The feedback control of claim 10 wherein said predetermined angle is parallel to said electric field.

12. The feedback control of claim 10 wherein said controller changes said electric potential by a value proportional to the difference between said current state signal and said reference signal.

13. The feedback control of claim 10 wherein said light source is a laser light source disposed on one side of said electrorheological fluid and wherein said means for detecting said light beam is a detector disposed on the opposite side of said electrorheological fluid.

14. The feedback control of claim 10 wherein said pair of spatially separated electrodes are a pair of electrically conductive transparent coatings disposed respectfully on the internal surfaces of a pair of spatially separated non-conductive transparent members.

15. The feedback control of claim 13 wherein said pair of spatially separated electrodes are a pair of spatially separated, electrically conductive opaque members, and where one of said pair of electrically conductive opaque members has a first aperture receiving said light source and the other of said pair of electrically conductive opaque members has a second aperture axially aligned with said first aperture receiving said photodetector.

16. The feedback control of claim 13 wherein said pair of spatially separated electrodes are a pair of electrically conductive opaque members having a window provided therethrough permitting said light beam to pass through said electrorheological fluid from said laser light source to said photodetector.

17. A method for changing the response time of an electrorheological fluid comprising the steps of:

measuring at least one parameter of the electrorheological fluid to generate a current state signal indicative of the current state of the electrorheological fluid;

generating a reference signal having a value corresponding to a desired state of the electrorheological fluid;

changing the value of an electric field applied across the electrorheological fluid as a function of the difference between said current state signal and said reference signal until said current state signal is equal to said reference signal indicating said current state of said electrorheological is precisely equal to said desired state of the electrorheological fluid.

18. The method of claim 17 wherein said step of measuring at least one parameter measures the optical transmission of said electrorheological fluid in an direction parallel to said electric field.

19. The method of claim 18 wherein said step of measuring the optical transmission comprises the steps of:

generating a light beam of known intensity through said electrorheological fluid parallel to said electric field;

detecting the intensity of said light beam with a photodetector after being transmitted through said electrorheological fluid to generate said current state signal.

20. The method of claim 19 wherein said step of generating a light beam generates a laser light beam.

21. The method of claim 17 wherein said step of measuring at least one parameter measures the optical reflectivity of said electrorheological fluid.

22. A method for increasing the response of an electrorheological fluid from a current state to a desired state comprising the steps of:

directing a light beam of a known intensity through said electrorheological fluid at a predetermined angle relative to the electric field placing said electrorheological fluid in said current state;

detecting the intensity of said light beam after reacting with said electrorheological fluid to generate a current state signal;

generating a reference signal having a value corresponding to a desired state of said electrorheological fluid;

changing the value of the electric field applied across said electrorheological fluid as a function of the difference between said current state signal and said reference signal to reduce the response of said electrorheological fluid from said current state to said desired state.

23. The method of claim 22 wherein said step of changing the value of the electric field changes said value of said electric field by an amount proportional to the difference between said current state signal and said reference signal.

24. The method of claim 22 wherein said step of detecting detects the intensity of said light beam being transmitted through said electrorheological fluid.

25. The method of claim 22 wherein said step of detecting detects the intensity of said light beam reflected from the surface of said electrorheological fluid.

* * * * *